United States Patent [19]
Boucher

[11] 3,938,514
[45] Feb. 17, 1976

[54] BLADDER WASH METHOD AND APPARATUS

[76] Inventor: Lionel J. Boucher, 747 Thibault, Sainte Therese, Quebec, Canada

[22] Filed: July 18, 1974

[21] Appl. No.: 489,717

[52] U.S. Cl. ............................... 128/232; 222/206
[51] Int. Cl.² ........................................... A61M 1/00
[58] Field of Search .......... 128/232, 231, 230, 278, 128/260, 245, 240, 241, 349; 222/92, 107, 215, 206

[56] References Cited
UNITED STATES PATENTS

| | | | |
|---|---|---|---|
| 3,058,627 | 10/1962 | Eskridge | 128/278 UX |
| 3,154,078 | 10/1964 | Goodrich, Jr. | 128/349 B |
| 3,172,577 | 3/1965 | Hartung | 222/206 |
| 3,211,151 | 10/1965 | Foderick et al. | 128/349 B |
| 3,266,532 | 8/1966 | Stewart | 128/232 X |
| 3,329,147 | 7/1967 | Barron | 128/230 |
| 3,481,334 | 12/1969 | Diskin et al. | 128/240 X |
| 3,527,203 | 8/1970 | Gravlee | 128/241 X |
| 3,557,788 | 1/1971 | Swartz | 128/232 |
| 3,626,928 | 12/1971 | Hohokus et al. | 128/241 X |
| 3,780,736 | 12/1973 | Chen | 128/231 |

Primary Examiner—Richard A. Gaudet
Assistant Examiner—J. Yasko
Attorney, Agent, or Firm—Cushman, Darby & Cushman

[57] ABSTRACT

A method and apparatus for washing the bladder of a patient with an indwelling catheter. The method comprises introducing the tip of a prefilled bladder washing device into the catheter, expelling the liquid from the device to the bladder, latching the device in its compressed position, maintaining the liquid in the bladder a predetermined amount of time and then unlatching the device, withdrawing the previously introduced liquid thereinto, and disposing of the device. Asepsis is assured by the present method. The apparatus has guiding and expansion and contraction means associated therewith as well as latching means that do not interfere with the operation of the device yet assures secure latching in the compressed position.

12 Claims, 5 Drawing Figures

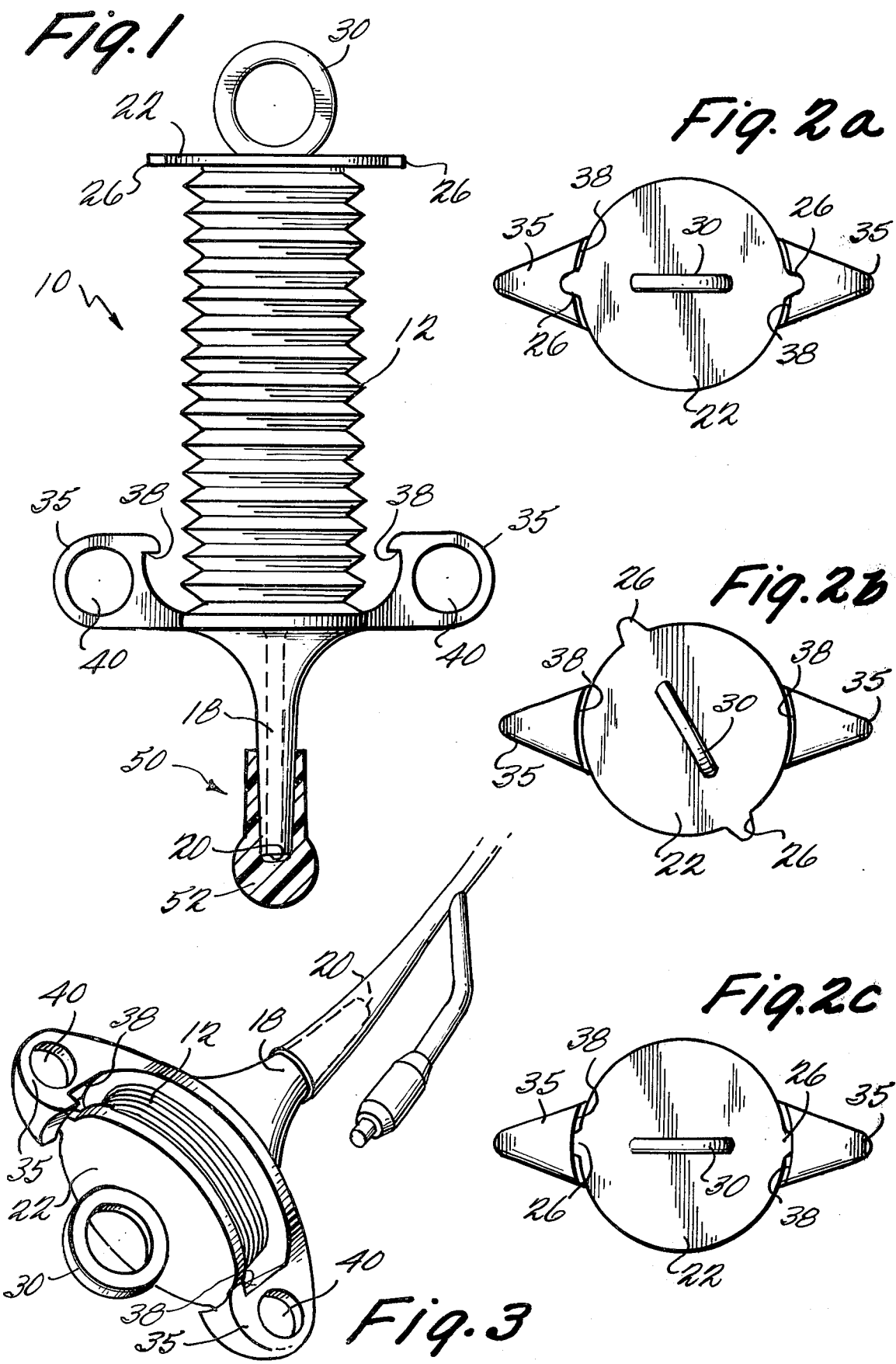

BLADDER WASH METHOD AND APPARATUS

BACKGROUND AND SUMMARY OF THE INVENTION

The invention relates to a method and apparatus for bladder irrigation. At the present time there exist no commercially acceptable methods and apparatus for aseptically washing the bladder of an individual with an indwelling catheter. The typical prior art procedure for bladder irrigation — and example of which is set forth in pages D-1 to D-3 of Publication No. PKST 1035 of Pharmaseal Laboratories of Glendale California — has been to remove the drainage tube from an indwelling catheter, fill, a disposable bulb-type or disposable piston syringe with a medication prescribed by a doctor [usually Neosporine], insert the syringe into the catheter and slowly inject it, clamp off the catheter, fill the syringe with irrigation fluid, insert the tip of the syringe into the catheter, remove the catheter clamp, inject the fluid, clamp off the catheter, refill the syringe again and repeat the procedure as many times as is necessary to substantially fill the bladder with irrigation liquid [usually about 150–200 cc; the syringes used are most often 50cc], after the final fill clamp off the catheter and allow the irrigation liquid to remain in the bladder the prescribed length of time and then remove the clamp and allow the fluid to drain into a disposable collecting basin, and reattach the drainage tube. To insure asepsis, if the syringe is ever laid down during the filling operations, it must be placed on a sterile surface. No matter what precautions are taken however, it is virtually impossible to prevent at least some air from being admitted to the bladder during the repeated refilling operations.

According to the method and apparatus of the present invention, a bladder may be washed completely aseptically. According to the method of the present invention, a prescribed medication may be introduced through the tip of a prefilled bladder washing device, mixing taking place in the washing device. The tip cover covering the tip of the bladder washing device is then removed and the tip of the device inserted into the catheter. The device has been prefilled to contain the amount of solution necessary to wash the bladder completely, The device is then compressed, introducing the liquid into the bladder. When the device has been substantially completely compressed, the device is locked in that position. After the passage of the prescribed length of time, the device is unlocked and expanded, whereby the fluid contained within the bladder is withdrawn into the body of the device. When withdrawal is complete, the device is removed from the catheter, capped again with its original cover, and disposed of.

As is readily apparent, the method and apparatus of the present invention have many advantages over the prior art method and apparatus. The main advantage of the method of the present invention is of course that there is virtually no chance of air or any contaminants being introduced into the bladder as a result of the bladder irrigating process. The method of the present invention is truly aseptic. Also, the time for performing bladder washing is reduced by the method of the present invention; there are no time-consuming syring filling and catheter clamping procedures. Fewer items need to be handled, thus resulting in a more simplified handling procedure. Since substantially the same amount of liquid will of necessity be withdrawn from the bladder as was introduced therein by the washing procedure, there is no chance of bladder collapse due to the withdrawal of too much liquid. Also, the medication can be introduced with the irrigating solution, thus they will be properly mixed before reaching the bladder and will have their maximum effectiveness. [there will be no concentrated medication introduced which might not have the desired effects or reach all the areas required]. Also with this method a mechanical bladder washing can be utilized in addition to the washing that results just from the presence of the solution by introducing and withdrawing the liquid alternately. Also, because the method is so aseptic, the need for an antibiotic medication to reduce the chances of infection might be obviated.

The apparatus of the present invention also has numerous advantages over prior art devices. Since only one element is needed, obviously space will be saved for storage purposes. The device is less expensive to manufacture than the composite equipment that it replaces [usually a disposable syringe, disposable collecting tray, disposable graduate with cover, and sterile field are necessary for prior art methods]. Also the device preferably has means thereon for guiding the tip portion of the device into the catheter and holding it steady while the fluid is being expelled therefrom, and means for facilitating expansion of the device to draw the liquid into it. The device is prefilled so that the chances of a mistake being made in the introduction of a particular volume of liquid will be reduced, and a syringe filling operation will not be necessary.

In the preferred embodiment of the bladder washing device according to the teachings of the present invention, the device is bellows-like for easy and effective expansion and compression, and the lock for locking the device in a compressed position is designed to securely hold the device in place while not interfering at all with the operation thereof. Prior art devices generally concerned with the introduction and drawing of liquids have not had the positive desirable features of the present invention which result in its suitability for a bladder washing operation [see U.S. Pat. No. 3,387,610, 2,428,577, 3,557,788 and 3,747,812 for example].

It is the principle object of this invention to provide a bladder irrigation method and apparatus that assures asepsis and does not have any of the other drawbacks of prior art devices. This and other objects of the invention will become clear from an inspection of the detailed description of the invention and the appended claims.

BRIEF DESCRIPTION OF THE DRAWINGS

FIG. 1 is a side view of an exemplary pre-filled bladder washing device according to the teachings of the present invention;

FIGS. 2a through 2c are top views of the device shown in FIG. 1 in various stages of compression thereof; and;

FIG. 3 is a perspective view of the bladder washing device shown in FIG. 1 in place in a catheter and in its locked position.

DETAILED DESCRIPTION OF THE INVENTION

Preferred apparatus for practicing the method of the present invention is shown generally at 10 in FIG. 1. The bladder washing device 10 is composed of four main parts; a hollow prefilled body member 12, a tubular tip member 18, a removable cover 50 for tip 18, and cooperating locking portions, 38, 26, for locking the body member 12 in a compressed position thereof.

As shown in the drawings the body member 12 consists of a hollow structure prefilled with a suitable bladder irrigation fluid — such as normal saline, Ringer solution, sterilized water etc. The bellows member 12 is expandable and compressable to vary the volume of liquid that may be contained therein. Under many circumstances, when following a bladder washing procedure, a certain volume of medication must be introduced into the bladder along with the liquid contained in the member 12. Provision is made within the member 12 for accepting such an extra volume of medication by insuring that the member 12 is not completely expanded when it is prefilled with liquid at the factory. Thus there is room within the member 12 to receive medication introduced therein through tip cover 50 (as will be explained more clearly below), and premixing of the medication and the prefilled liquid occurs.

A tubular tip portion 18, having an opening 20 throughout the length thereof, is attached to one end of the member 12, and is in fluid communication therewith. The liquid within the member 12 is thus expelled through the opening 20 in tip 18 when the member 12 is compressed, and liquid is drawn into the member 12 through the tip 18 when the member 12 is expanded. The tip 12 may be of any desired configuration as long as it corresponds to the configuration of the catheter to which it is to be connected in fluid engagement. A Luer tip would be preferred under many circumstances.

A means 50 is provided for covering the tip 18 after the member 12 has been prefilled and before use thereof. As shown in the drawings, the means 50 is a clear latex tip cover having a portion 52 thereof shaped so that it may be easily grasped by a thumb and finger for easy removal however, other tip configuration may be employed. Medication may be injected directly through the tip cover 50 by a needle tip syringe, or the cover 50 may be removed and the medication aseptically inserted into the body 12 via a Luer tup of a syringe which cooperates with the passage 20 through the tip portion 18. If desirable, the interior portion of the cover 50 may be sized so that if fits over the drainage tube that will be removed from an indwelling catheter before the irrigating fluid may be introduced by the device 10.

Attached to the "top" portion of the bellows member 12 is a plate 22, terminating the end of the member 12, which plate 22 has locking projections 26 extending therefrom. These locking projections 26 cooperate with locking portion 38 of the member 35 terminating the other end of the body 12, as will be more fully explained hereinafter. Located on top of the plate 22 is a ring 30 adapted to receive the thumb of a person using the bladder washing device 10, whereby compression and expansion of the member 12 are facilitated.

Terminating the other end of the member 12 is the member 35. Member 35 has locking surfaces 38 formed therein for cooperation with the locking projections 26 of plate 22, and has a pair of ring-like portions 40 adapted to receive two fingers of an individual using the bladder washing device 10. By inserting one's fingers into the ring portions 40, guidance of the tip 18 of the device 10 into a catheter is facilitated as well as steadying of the device while the bellows member 12 is being compressed or expanded. The rings 40 and locking surfaces 38 are so positioned that the device 10 can be positively latched in place while the operation of the device is not hindered.

As seen most clearly in FIGS. 2a–2c, when the device 10 is being used, and it is desired to compress the body member 12 and introduce the liquid contained therein into a bladder, the member 12 is compressed until the portions 26 of plate 22 abut or are just above the portion 35. Then the whole device 12 is twisted — as shown in FIG. 2b — until projections 26 are out of the path of engagement with the portion 35. Then the member 12 is further compressed, and the projections 26 are allowed to return to their normal position wherein they will engage the undersurfaces 38 of the portion 35 — as shown in FIG. 2c. A view of the device 10 in this locked position while inserted in a catheter 60 is shown in FIG. 3.

Since the bellows member 12 is preferably constructed of resilient plastic rubber or other resilient material, it will tend to return to its original shape — as shown in FIG. 1 — after the locking portions 26, 38 for holding it into its locked position have been released. However, the normal resilient action will not be large enough to completely return it to its normal position and draw the liquid that had been introduced into the bladder back into the member 12; thus, the operator will use the ring portion 30 to pull up on the member 12 to expand it. Since the member 12 will be able to hold only substantially as much liquid as it had therein when it was prefilled and had the medication introduced therein, there will be virtually no possibility for too much liquid being withdrawn from the bladder so that bladder collapse would ensue. Alternatively, in cases where it is anticipated that there will be a large amount of excess liquid in the bladder when the bladder washing operation has been completed (such as when the device 10 remains locked for a long period of time, such as 45 minutes), provision can be made for this by prefilling and capping the member 12 at the factory while in a significantly compressed position. While this will not result in the introduction of any air into the system, it will allow enough room for medication that is to be introduced and for any excess liquid to be withdrawn from the bladder.

Although the apparatus has been shown in the drawings in what is presently conceived to be the most practical embodiment, it will be apparent to one of ordinary skill in the art that the method of the present invention may be practiced with other apparatus than that shown. For instance, different types of guiding means may be provided other than rings 40, a different means for facilitating compression and expansion of the member 12 may be provided other than the ring 30, different types of tips and tip covers may be provided, different locking positions could be used, and even a different type of volume expansion and contraction member may be provided than the bellows 12 (such as a piston and cylinder or a bulb) — a bellows such as 12 is preferred however for ease of handling, ease of prefilling to the desired amount of inexpensive manufacture and the positive suction and expelling forces obtainable therewith.

The bladder washing operation of the present invention generally comprises the following main steps: The prescribed medication (if any — the need for antibiotics may be obviated by the use of the aseptic system of the present invention) is introduced into the bladder washing device, the drainage tube is removed from the patient's indwelling catheter, and the tip cover of the bladder washing device is removed. Then a sealed airtight communication is made between the tip of the device and the catheter, the prefilled volume of liquid in the device is introduced into the bladder via the catheter, the solution is maintained in the bladder for the prescribed length of time [which is usually about 20 – 30 minutes, but can be longer or only instantaneous] while the seal is maintained, and the solution is withdrawn while the seal is maintained. After withdrawal of the liquid — and only then — the seal is broken, and the device disposed of.

A detailed step-by-step procedure for practicing the present invention is as follows:

A. Check to see that the patient has an indwelling clean catheter, and aseptically disconnect the drainage tubing and drainage bag from the catheter.

B. Add the prescribed medication to the device 10 by injecting it through the tip cover 50 into the opening 20 through the tip 18. The medication and the prefilled liquid should then be mixed properly.

C. Remove the tip cover 50 from the tip 18, and either place the tip 50 on a flat surface for further use, or place it over the open end of the drainage tube that has been disconnected.

D. By grasping the rings 40 for guidance, insert the tip 18 into a female adapter of the catheter 60, thereby forming a seal between the tip 18 and the catheter 60 that is air-tight.

E. Still holding the rings 40 with the fingers, and inserting the thumb in the ring 30, compress the member 12 thereby expelling the liquid therefrom into the catheter.

F. If it is desired to mechanically wash the bladder in addition to introducing the irrigating liquid therein, the liquid will be withdrawn immediately after introduction by holding the rings 40 while pulling up on the ring 30 and then again introducing the liquid by pressing down on ring 30. This procedure may be repeated as many times as necessary, and no air will be introduced thereby since the seal between the tip 18 and the catheter 60 will still be maintained. The liquid should not be introduced as rapidly as is possible, otherwise injury to the patient may result. There is no need to hold the device 10 as carefully as prior art devices to insure that air will not be introduced since the device is prefilled.

G. After mechanical washing, if it is desired to hold the liquid within the bladder a predetermined amount of time, the bellows 12 is compressed until the projections 26 on plate 22 abut or are just above the portion 35, then the bellows 12 are twisted by twisting ring 30 and plate 22, the bellows 12 are further depressed, and the twisting force is relieved so that the projections 26 will engage the locking surfaces 38 of the portion 35. The device 10 will then stay in this latched position with the seal between the tip 18 and the catheter 60 maintained the prescribed amount of time.

H. When the time has passed, the device 10 is unlocked by again twisting ring 30 and plate 22 so that the projections 26 no longer engage the surfaces 38, the bellows 12 are expanded slightly (they will do so by themselves to a certain extent) by pulling up on the ring 30, the twisting force is relieved, and while holding the rings 40 the ring 30 is slowly pulled up whereby all the liquid previously introduced into the bladder will be drawn into the member 12.

I. After the member 12 is filled — and only then — the seal between the tip 18 and the catheter 60 is broken, and the drainage tube is attached to the catheter again.

J. The tip cover 50 may be again placed on the tip 18 of the device 10, and the device is disposed of. Note that as a result of practicing the present invention, this is the only thing that need be disposed of instead of a syringe, collecting tray, graduate with cover, and sterile field as is necessary when practicing the prior art procedures for bladder washing.

To provide for versatility in the type of bladder washing and irrigating procedures that will be employed, prefilled devices 10 may be provided in various sizes - usually a 150 cc and a 200 cc size. As mentioned above, it may also be desirable where the device will be left in longer than the normal 20–30 minutes of dwell time to provide a device 10 that has a potential volume a predetermined amount (such as 50cc) larger than the volume of irrigation solution to be used, and to fill the bellows 12 while the bellows are contracted that predetermined amount, and then to cap the tip 18 with the cover 50. Then more liquid can be withdrawn thereby than introduced therewith. Provision can always be made for the introduction of medication.

It will be readily apparent to one of ordinary skill in the art that a bladder washing method and apparatus have been herein disclosed that insure asepsis during a bladder washing prodedure, and have all of the other advantages mentioned over the methods and apparatus of the prior art. While the invention has been herein disclosed in what is presently conceived to be the most practical and preferred embodiments, it is to be understood that many modifications may be made therefrom within the scope of the invention; thus it is intended that the method and apparatus of the present invention cover all equivalents thereto within the scope of the invention, which scope is to be restricted only by the appended claims.

What is claimed is:

1. Apparatus for aseptically washing the bladder of an individual having an indwelling catheter, said apparatus comprising a. means for aseptically washing a bladder, for facilitating mechanical washing action of liquid in washing a bladder, and for preventing removal of too much liquid from a bladder, said means comprising (i) a hollow body member having the interior thereof prefilled with a predetermined amount of liquid for washing a bladder, and having first and second ends thereof, (ii) a tubular tip portion extending from said hollow body member at the first end thereof and adapted to be attached to said catheter to allow liquid communication between the bladder and the hollow body member but to prevent air from being admitted thereto, (iii) means for contracting and expanding the volume of said body member from a first position wherein said body member is prefilled with liquid, to a second position wherein substantially all of said liquid is expelled from said body member, to a third position wherein said liquid is drawn back into said body member and said body member is substantially filled, and (iv) means for releasably locking said body member in said second position thereof wherein said volume thereof is contracted and the prefilled liquid therein is substantially expelled therefrom, said means including a plate having a pair of projections thereon, said plate terminating the second end of said body member and located exteriorly of said body member, and a pair of locking surfaces, said locking surfaces being spaced from but adjacent to the first end of said body member, said locking surfaces being disposed in the path of movement of said projections of said plate as said body member is moved from said first to said second position, said body member being twistable so that said projections may be moved out of interferring relationship with said locking surfaces, and after having moved past said locking surfaces said body member being twistable back into its normal path of movement so that said plate projections abut said locking surfaces whereby said body member assumes said second position whereby movement of said body member from said second position to said third position is prevented, and b. means for maintaining said prefilled volume of liquid within said body member until use thereof.

2. Apparatus as recited in claim 1 further comprising means for facilitating guidance of said tip portion into liquid communicating air-tight relationship with said catheter.

3. Apparatus as recited in claim 1 further comprising means for facilitating contraction and expansion of said volume of said hollow body member.

4. Apparatus as recited in claim 3 wherein said means includes a ring adapted to be engaged by a thumb, said ring attached to a portion terminating said body member at the end thereof spaced from said tip portion.

5. Apparatus as recited in claim 1 wherein said means for maintaining said prefilled volume of liquid within said body member until use thereof includes a cover for said tip portion made of resilient material.

6. Apparatus as recited in claim 1 wherein said body member comprises a bellows having two open ends, and a means for terminating each of said open ends of said bellows.

7. Apparatus as recited in claim 1 wherein said apparatus is prefilled to less than its maximum liquid containing volume, provision thereby being made for introduction of a volume of medication or for withdrawal of an amount of fluid in excess of the amount that was introduces into said bladder.

8. Apparatus for aseptically washing the bladder of an individual having an indwelling catheter, said apparatus comprising a. means for aseptically washing a bladder, for facilitating mechanical washing action of liquid in washing a bladder, and for preventing removal of too much liquid from a bladder, said means comprising (i) a hollow body member prefilled with a predetermined amount of liquid for washing a bladder, (ii) means for contracting and expanding the volume of said hollow body member to alternately expell liquid from and draw liquid into said body member, (iii) means located exteriorly of said body member for locking said body member in a position thereof wherein said volume thereof is contracted and the prefilled liquid therein is substantially expelled therefrom and (iv) a tubular tip portion extending from said hollow body member and adapted to be attached to said catheter to allow liquid communication between the bladder and the hollow body member but to prevent air from being admitted thereto, b. means for maintaining said prefilled volume of liquid within said body member until use thereof.

c. means for facilitating guidance of said tip portion into liquid communicating air-tight relationship with said catheter, said means comprising a pair of rings mounted on a portion terminating said body member adjacent said tip.

9. A method of aseptically washing the bladder of an individual having an indwelling catheter, said method comprising the steps of a. attaching the tip of a bladder washing device prefilled with bladder washing liquid in air-tight liquid communication with the indwelling catheter, b. reducing the volume of said bladder washing device to cause said liquid therein to enter the catheter and bladder, c. latching said bladder washing device in a reduced volume position, d. maintaining said bladder washing device in its latched position a predetermined amount of time, e. withdrawing said solution from said bladder by unlocking said bladder washing device and expanding the volume thereof, and f. removing said bladder washing device from attachment with the catheter.

10. A method as recited in claim 9 comprising the further step of introducing a predetermined amount of medication into said bladder washing device without allowing the entrance of air therein before attaching the tip of said device to said catheter.

11. A method as recited in claim 9 comprising the further step of disposing of said bladder washing device after use thereof.

12. A method as recited in claim 9 comprising the further steps of repeatedly alternately reducing and expanding the volume of said bladder washing device before locking it in a compressed position.

* * * * *